US006730804B1

(12) United States Patent
Kaufhold et al.

(10) Patent No.: US 6,730,804 B1
(45) Date of Patent: May 4, 2004

(54) PROCESS FOR PREPARING CYCLOPROPANECARBOXYLATES OF LOWER ALCOHOLS

(75) Inventors: Manfred Kaufhold, Marl (DE); Marcel Feld, Cologne (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/141,163

(22) Filed: Aug. 27, 1998

(30) Foreign Application Priority Data

Sep. 1, 1997 (DE) .......................... 197 38 072

(51) Int. Cl.⁷ .............................. C07C 69/74
(52) U.S. Cl. ........................ 560/124; 560/102
(58) Field of Search ................. 560/124, 102

(56) References Cited

U.S. PATENT DOCUMENTS

| | | | | |
|---|---|---|---|---|
| 3,567,740 A | * | 3/1971 | Matsui et al. | 549/499 |
| 3,671,548 A | * | 6/1972 | Itaya et al. | 549/79 |
| 3,673,237 A | * | 6/1972 | Janiak | 560/124 |
| 3,876,682 A | * | 4/1975 | Henrick et al. | 560/124 |
| 3,981,903 A | * | 9/1976 | Hirano et al. | 560/124 |
| 5,504,245 A | | 4/1996 | Liang et al. | 562/506 |

FOREIGN PATENT DOCUMENTS

WO        WO 94/01389    *   1/1994

OTHER PUBLICATIONS

Saam, Low–temperature Polycondensation of Carboxylic Acids and Carbinols in Heterogeneous Media, Jan. 1998, 36(2).; p. 341–356.*

Kirk–Othmer, Esterification, Encyclopedia of Chemical Technology, 3 rd ed., vol. 9: p. 291–308, Apr. 17, 1980.*

Derwent Abstracts, SU 322 986, Apr. 5, 1976.

K. W. F. Kohlrausch, et al., Monatsh. Chem, vol., 70, pp. 377,378, 395 and 396, "Studien Zum Ramaneffekt", 1937.

James J. Folmer, et al., Tetrahedron Letters, vol., 34, No. 17, pp. 2737 to 2740, "Generation of Esters from Carboxylic Acids Using Appel's Salt (4,5–Dichloro–1,2,3–Dithiazolium Chloride)", 1993.

Kazuhiko Saigo, et al., Bulletin of the Chemical Society of Japan, vol. 50, No. 7, pp. 1863 to 1866, "New Method for the Preparation of Carboxylic Esters", 1977.

Hans Beyer, Handbook of Organic Chemistry, pp. 356 and 357, "Lehrbuch der Organischen Chemie", 1968.

* cited by examiner

Primary Examiner—D. Margaret Seaman
Assistant Examiner—Taylor V Oh
(74) Attorney, Agent, or Firm—Oblon, Spivak, McClelland, Maier & Neustadt, P.C.

(57) ABSTRACT

Cyclopropanecarboxylates of lower alcohols are prepared by esterification of the corresponding cyclopropanecarboxylic acids with the corresponding lower alcohols in the presence of an acid catalyst, while maintaining a considerable stoichiometric excess of the cyclopropanecarboxylic acid with respect to the lower alcohol, keeping the temperature at from 100 to 200° C. and distilling off the cyclopropanecarboxylate together with the water of reaction and small amounts of alcohol. Cyclopropanecarboxylates of lower alcohols are valuable intermediates in the pharmaceutical and agrochemical sectors.

19 Claims, No Drawings

PROCESS FOR PREPARING CYCLOPROPANECARBOXYLATES OF LOWER ALCOHOLS

BACKGROUND OF THE INVENTION

1. Field of the Invention

The invention relates to a process for preparing cyclopropanecarboxylates of lower alcohols by esterification of the carboxylic acids with the lower alcohols.

2. Discussion of the Background

Cyclopropanecarboxylates of lower alcohols have recently achieved considerable significance as intermediates in the synthesis of pharmaceuticals and pesticides. This has partly been due to the fact that cyclopropanecarboxylic acid has more recently become readily available by oxidation of the corresponding aldehyde (see U.S. Pat. No. 5,504,245) and is being produced industrially. However, there has hitherto been no satisfactory process for preparing these esters.

The esterification of carboxylic acids with an alcohol with the liberation of water is a known reaction which leads to an equilibrium. The equilibrium is usually attained more quickly using acid catalysts. Removal of the water of reaction using an entrainer and/or use of an excess of alcohol can shift the equilibrium in the direction of ester formation. This principle is applied in the process in the Patent Specification SU 322 986, in which cyclopropanecarboxylic acid is esterified at about 80° C. using a large excess of methanol in the presence of p-toluenesulfonic acid as catalyst, and toluene or carbon tetrachloride as entrainer for the water. However, the yield of 70% is unsatisfactory. Also, the entrainer introduces a further substance into the process.

Kohlrausch and Skrabal (Monatsh. Chem 70 [1937], 377,395) prepared methyl cyclopropanecarboxylates by esterifying the acid with methanol using concentrated sulfuric acid as catalyst. However, the resulting crude ester had to be distilled several times in order to obtain a pure product. Every additional distillation increases the cost and reduces the yield.

Folmer and Weinreb (Tetrahedron Lett. [1993] 34 (17), 2737–40) achieved relatively good yields of methyl cyclopropanecarboxylate by carrying out esterification at temperatures of from −78° C. to room temperature, but the auxiliaries they used, the so-called Appel salt (4,5-dichloro-1,2,3-dithiazolium chloride) and 2,6-dimethylpyridine, are expensive and difficult to dispose of.

These and other processes described in the literature operate at temperatures below 100° C. (e.g. Saigo, Kazihiko Saigo, Masahiro Usui, Kazumori Kikuchi, Eiichiro Shimada and Teruaki Mukayama, Bull. Chem. Soc. Jpn. [1977] 50 (7), 1863–6 at room temperature) and thus take into account the known thermal instability of cyclopropane compounds (see e.g. Hans Beyer, Lehrbuch der Organischen Chemie [Handbook of Organic Chemistry], publisher S. Hirzel, Leipzig, 15th/16th edition (1968), page 357). Most of the known processes operate with an excess of alcohol in the esterification zone. The processes have unsatisfactory yields, disadvantageously large numbers of stages and/or require auxiliaries which are expensive and difficult to dispose of.

SUMMARY OF THE INVENTION

It was therefor the object of the invention to provide a process which gives good yields, uses inexpensive auxiliaries and produces a product which can be purified in a simple manner.

This object is achieved by a process for preparing cyclopropanecarboxylates of lower alcohols by esterification of the corresponding cyclopropanecarboxylic acids with the corresponding lower alcohols in the presence of an acid catalyst, which comprises maintaining in the esterification zone a considerable stoichiometric excess of the cyclopropanecarboxylic acid with respect to the lower alcohol, keeping the temperature in the esterification zone at from 100 to 200° C. and distilling off, from the reaction zone, the cyclopropane carboxylate together with the water of reaction and small amounts of alcohol. The process according to the invention produces high purity esters in yields of more than 90%, based on reacted cyclopropanecarboxylic acid. Surprisingly, it is not necessary to operate under gentle conditions, i.e. at temperatures <100° C. The cyclopropanecarboxylic acid, which is sensitive to thermal stress, particularly in an acid medium, is exposed to these stress conditions for considerably longer than the alcohol, which is unproblematical in this respect, as the cyclopropanecarboxylic acid is present in considerable excess. Despite this, there are no secondary reactions, and traces of decomposition products have never been found. Because of the high temperatures, excellent space-time yields are also obtained. The process can be carried out batchwise or, with particular advantage, continuously.

In the process according to the invention, the unsubstituted cyclopropanecarboxylic acid or its ring-substituted derivatives, e.g. the cyclopropanecarboxylic acids ring-substituted by 1 or 2 alkyl radicals having 1 to 4 carbon atoms, are reacted.

The cyclopropanecarboxylates of lower alcohols are useful in the synthesis of pharmaceuticals and pesticides.

DESCRIPTION OF THE PREFERRED EMBODIMENTS

Preferred lower alcohols are those whose boiling point does not differ greatly from that of water at atmospheric pressure, i.e. in the region of 100±about 40° C. Preferred lower alcohols are alkanols having 1 to 4 carbon atoms, such as ethanol, n-propanol, i-propanol, n-butanol and, in particular, methanol.

Suitable esterification catalysts are the known acid catalysts, such as sulfuric acid; sulfonic acid group-containing ion exchange resins; sulfonic acids, such as methanesulfonic acid, higher alkanesulfonic acids, benzenesulfonic acid, p-toluenesulfonic acid and, in particular, higher alkybenzenesulfonic acids, preferably those having branched or unbranched $C_{10}$- to $C_{13}$-alkyl radicals. The amount of catalysts used is generally such that their proportion in the esterification zone is from 0.1 to 10 percent by weight.

The process of the invention is advantageously carried out at a temperature of from 120 to 200° C., preferably between 130 to 150° C. It is generally carried out at atmospheric pressure. Elevated pressure is recommended if the process is to be carried out at a temperature at which the cyclopropanecarboxylic acid is gaseous under atmospheric pressure (un-substituted cyclopropanecarboxylic acid boils at 182° C.). Reduced pressure can be applied when a relatively high-boiling lower alcohols, such as n-propanol, is used.

An important feature of the process according to the invention is that there is a considerable stoichiometric excess of cyclopropanecarboxylic acid with respect to the lower alcohol in the esterification zone. As a rule, the cyclopropanecarboxylic acid is present in an amount of from 2 to 1000, preferably 10 to 200, times the stoichiometric quantity. When the process is carried out batchwise, the lower alcohol can, for example, be introduced gradually on its own into the initial charge of cyclopropanecarboxylic acid, or alternatively in the form of a mixture with further cyclopropanecarboxylic acid, the proportion thereof being less than that of the ester produced in the esterification zone. In both cases, the initial charge of cyclopropanecarboxylic acid is consumed at a more or less rapid rate. Lower alcohol which distills off with the water of reaction can be returned to the esterification. When the process is carried out continuously the cyclopropanecarboxylic acid is again initially charged and a mixture of cyclopropanecarboxylic acid and lower alcohol is added to it, the mixing ratio being chosen such that the amount of cyclopropanecarboxylic acid introduced corresponds to the ester which is produced in the reaction zone and distills off, so that a steady state prevails in the reaction zone. That is generally the case when the molar ratio of cyclopropanecarboxylic acid and lower alcohol, depending on the starting substances, is in the range from 1:1.20 to 1:1.02, advantageously from 1:1.10 to 1:1.05. The slight excess of lower alcohol distills off with the ester formed and the water of reaction.

The vapor mixture is condensed, and the condensate forms two phases. The upper, aqueous phase can be partially distilled to recover the lower alcohol contained therein and the resulting lower alcohol be returned to the esterification. Further distillation of the aqueous phase produces small quantities of ester which, after separation from the water which is co-distilled azeotropically, can also be returned to the esterification or can be worked up together with the lower, organic phase. The residue is waste water with few impurities, which can easily be disposed of.

The lower, organic phase is partially distilled in a similar way and thus separated from small amounts of water and lower alcohol. The residue is very pure cyclopropanecarboxylate which does not need to be distilled further for the majority of uses.

The following examples serve to illustrate in more detail the process according to the invention, but are not intended to limit its field of application as defined in the patent claims. All contents and percentages were determined by gas chromatography.

EXAMPLE 1

Methyl Cyclopropanecarboxylate

A glass apparatus is used which comprises a 5-necked flask fitted with stirrer, thermometer, dropping funnel, distillation column with mounted distillation bridge and inlet pipe reaching to the deepest point in the flask.

The flask is charged with 258.3 g (3 mol) of cyclopropanecarboxylic acid (CPC) and 10 g of $C_{10}$–$C_{13}$-alkylbenzenesulfonic acid (Marlon®AS 3 acid), and the mixture is heated to 140° C. A mixture of 430.5 g (5 mol) of cyclopropanecarboxylic acid and 173 g (5.4 mol) of methanol is then added each hour via the inlet pipe. These quantities of starting materials approximately correspond, after 13 hours, to the quantities of substances which distill off, so that the level remains almost constant.

403 g of distillate are obtained which divides into two phases, which are separated.

The upper, aqueous phase, 88 g, has the following composition:

| The upper, aqueous phase, 88 g, has the following composition: | |
|---|---|
| Water | 70.0% by wt. |
| Methanol | 24.4% by wt. |
| Methyl cyclopropane carboxylate (MCPC) | 5.4% by wt. |
| The lower, organic phase, 315 g, has the following composition: | |
| Water | 6.8% by wt. |
| Methanol | 7.1% by wt. |
| MCPC | 86.0% by wt. |
| 455 g of the following composition remained in the reaction flask: | |
| Water | 0.6% by wt. |
| MCPC | 29.1% by wt. |
| CPC and alkylbenzenesulfonic acid | 70.1% by wt. |

The yield of MCPC, based on reacted CPC, is 91% of theory. To purify the crude MCPC (315 g), the organic phase is only partially distilled, thus removing water and also methanol, which can be returned to the esterification. The residue produced is MCPC having a purity of 99.8%.

The aqueous phase is also only partially distilled, giving MCPC and methanol. The bottom product which remains is readily disposable waste water having a carbon content of 400 mg/l.

EXAMPLE 2

Ethyl Cyclopropanecarboxylate

The apparatus described in Example 1 is used and the following are employed:

258.3 g (3 mol) of cyclopropanecarboxylic acid 7 g of $C_{10}$–$C_{13}$-alkylbenzenesulfonic acid (Marlon®AS 3 acid).

The substances are combined and heated to 140° C. At this temperature, a mixture of 733 g (8.51 mol) of CPC and 423.6 g (9.19 mol) of ethanol is pumped in at a rate of 100 ml/h. The level initially rises, since the amount of distillate is less than the quantity pumped in. Increasing the temperature to 160° C. establishes a steady state. Homogeneous distillates having various water contents are produced:

| 1st distillate | 257 g | 20.7% by weight of water |
|---|---|---|
| 2nd distillate | 275 g | 12.7% by weight of water |
| 3rd distillate | 162 g | 0.5% by weight of water |

Distillates 1 and 2 are combined, and ethanol is distilled off as an azeotrope with water. The distillation residue consists of two phases, which can be easily separated by adding 7 g of sodium sulfate. The lower, aqueous phase is discarded. The upper phase, 254.8 g, is pure ethyl cyclopropane carboxylate. Complete distillation of the reactor bottom product gives a further 1.61 mol of ester. 5.68 mol of CPC remain as residue.

A total of 5.22 mol of ester are obtained. The yield is 89.5% of theory, based on reacted CPC.

EXAMPLE 3 n-Propyl Cyclopropanecarboxylate

The apparatus described in Example 1 is used and the following are employed:

317 g (3.68 mol) of cyclopropanecarboxylic acid 10 g of $C_{10}$–$C_{13}$-alkylbenzenesulfonic acid (Marlon®AS 3 acid)

The substances are combined and heated to 170° C. At this temperature, a mixture of 528.3 g (7.13 mol) of CPC and 462.8 g (7.7 mol) of ethanol are pumped in over the course of 10 hours. At the chosen high temperature of 170° C., the level in the reactor does not rise. The resulting distillate has the following composition:

89.9% by wt. of n-propyl cyclopropane carboxylate 3.2% by wt. of CPC 6.4% by wt. of n-propanol In this case, a relatively large amount of CPC is present in the distillate; this can be attributed to the high still temperature. Work-up is as described in Example 2. The n-propyl cyclopropanecarboxylate is obtained with a purity of 99.8% by weight in a yield of about 81% of theory, based on reacted CPC.

This application is based upon German Patent Application No. 197 38 072.7, filed on Sep. 1, 1997, the entire contents of which are herein incorporated by reference.

Having now fully described the invention, it will be apparent to one of ordinary skill in the art that many changes and modifications can be made thereto without departing from the spirit or scope of the invention as set forth herein.

What is claimed is:

1. A process for preparing a cyclopropanecarboxylate ester of a lower alcohol which comprises:

heating a stirred solution of a cyclopropanecarboxylic acid and an acid catalyst in a reactor at a temperature of from 100 to 200° C.;

adding to the bottommost part of the stirred solution a mixture of the cyclopropanecarboxylic acid and the lower alcohol or the lower alcohol alone; wherein the rate of adding is maintained at a level such that the mole ratio of the cyclopropanecarboxylic acid to the lower alcohol is maintained within the range of 2 to 1000;

esterifying the cyclopropanecarboxylic acid with the lower alcohol in the presence of the acid catalyst in the reactor; and distilling off the cyclopropanecarboxylate ester together with the water of reaction and small amounts of the lower alcohol.

2. The process as claimed in claim 1, wherein the temperature is maintained in the range of from 120 to 200° C.

3. The process as claimed in claim 1, wherein the temperature is maintained in the range of from 130 to 150° C.

4. The process as claimed in claim 1, wherein the acid catalyst is selected from the group consisting of sulfuric acid, an ion exchange resin containing sulfonic acid groups and a sulfonic acid.

5. The process as claimed in claim 4, wherein the sulfonic acid is a higher alkylbenzenesulfonic acid having a branched or unbranched $C_{10}$- to $C_{13}$-alkyl radical.

6. The process as claimed in claim 1, wherein the mole ratio of the cyclopropanecarboxylic acid to the lower alcohol is from 10 to 200.

7. The process as claimed in claim 1 wherein said lower alcohol is selected from the group consisting of ethanol, n-propanol, isopropanol, n-butanol and methanol.

8. The process as claimed in claim 4, wherein the catalyst is present in an amount of 1–10% by weight based on the cyclopropanecarboxylic acid and the lower alcohol.

9. The process as claimed in claim 2, wherein the acid catalyst is selected from the group consisting of sulfuric acid, an ion exchange resin containing sulfonic acid groups and a sulfonic acid.

10. The process as claimed in claim 3, wherein the acid catalyst is selected from the group consisting of sulfuric acid, an ion exchange resin containing sulfonic acid groups and a sulfonic acid.

11. The process as claimed in claim 9, wherein the acid catalyst is a sulfonic acid, which is a higher alkylbenzenesulfonic acid having a branched or unbranched $C_{10}$- to $C_{13}$-alkyl radical.

12. The process as claimed in claim 10, wherein the acid catalyst is a sulfonic acid, which is a higher alkylbenzenesulfonic acid having a branched or unbranched $C_{10}$- to $C_{13}$-alkyl radical.

13. The process as claimed in claim 5, wherein the sulfonic acid is present in an amount of 0.1–10% by weight based on the cyclopropanecarboxylic acid and the lower alcohol.

14. The process as claimed in claim 1, wherein the acid catalyst is present in an amount of 0.1–10% by weight based on the cyclopropanecarboxylic acid and the lower alcohol.

15. The process of claim 1, wherein the process is continuous.

16. The process of claim 15, wherein the mole ratio of the mixture of the cyclopropanecarboxylic acid to the lower alcohol is from 1:1.20 to 1:1.02.

17. The process of claim 11, wherein the mole ratio of the mixture of the cyclopropanecarboxylic acid to the lower alcohol is from 1:1.10 to 1:1.05.

18. The process of claim 11, wherein the sulfonic acid is present in an amount of 0.1–10% by weight based on the cyclopropanecarboxylic acid and the lower alcohol.

19. The process of claim 12, wherein the sulfonic acid is present in an amount of 0.1–10% by weight based on the cyclopropanecarboxylic acid and the lower alcohol.

* * * * *